(12) United States Patent
Zou et al.

(10) Patent No.: US 10,407,379 B2
(45) Date of Patent: *Sep. 10, 2019

(54) DERIVATISATION OF CARBON

(71) Applicant: SCHLUMBERGER TECHNOLOGY CORPORATION, Sugar Land, TX (US)

(72) Inventors: Fenglou Zou, Calgary (CA); Nathan Lawrence, Cambridge (GB); Timothy Jones, Cambridge (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/665,832

(22) Filed: Mar. 23, 2015

(65) Prior Publication Data

US 2015/0197481 A1  Jul. 16, 2015

Related U.S. Application Data

(63) Continuation of application No. 13/142,515, filed as application No. PCT/IB2010/000293 on Feb. 12, 2010, now abandoned.

(30) Foreign Application Priority Data

Mar. 20, 2009 (GB) .................................. 0904813.3

(51) Int. Cl.
*B82Y 30/00* (2011.01)
*B82Y 40/00* (2011.01)
(Continued)

(52) U.S. Cl.
CPC ............ *C07C 201/12* (2013.01); *B82Y 30/00* (2013.01); *B82Y 40/00* (2013.01); *C01B 32/156* (2017.08);
(Continued)

(58) Field of Classification Search
CPC ..... B82Y 30/00; B82Y 40/00; C01B 31/0273; C01B 31/04; C01B 32/28; C01B 32/354;
(Continued)

(56) References Cited

U.S. PATENT DOCUMENTS 5,223,117 A    6/1993  Wrighton et al.
5,739,376 A *  4/1998  Bingel .................. C07C 49/553
                                            540/467
(Continued)

FOREIGN PATENT DOCUMENTS

GB    2420849 A     6/2006
JP    2000247618 A  9/2000
(Continued)

OTHER PUBLICATIONS

Leffek (Canadian Journal of Chemistry, Basicity of substituted 2-phenyl-1,1,3,3-tetramethylguanidines and other bases in acetonitrile solvent, 1988, p. 590-595).*

(Continued)

*Primary Examiner* — Amy C Bonaparte

(57) ABSTRACT

A molecular species is covalently attached to elemental carbon by exposing the carbon to a reaction mixture containing a strong base and a compound of the formula

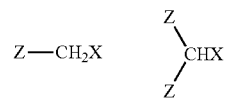

or
in which X denotes a covalently attached atom or group capable of forming an X⁻ anion and each Z is a moiety comprising a plurality of atoms, but which does not have a hydrogen atom directly attached to the atom which itself is (Continued)

directly attached to the —CH$_2$X or —CHX group. The carbon substrate may be graphite or carbon nanotubes.

12 Claims, 5 Drawing Sheets

(51) Int. Cl.

| | | |
|---|---|---|
| C01B 32/20 | (2017.01) | |
| C01B 32/21 | (2017.01) | |
| C01B 32/28 | (2017.01) | |
| G01N 27/30 | (2006.01) | |
| C01B 32/156 | (2017.01) | |
| C01B 32/174 | (2017.01) | |
| C01B 32/194 | (2017.01) | |
| C01B 32/354 | (2017.01) | |
| C07C 201/12 | (2006.01) | |
| C01B 31/02 | (2006.01) | |
| C01B 31/04 | (2006.01) | |

(52) U.S. Cl.
CPC .......... *C01B 32/174* (2017.08); *C01B 32/194* (2017.08); *C01B 32/20* (2017.08); *C01B 32/21* (2017.08); *C01B 32/28* (2017.08); *C01B 32/354* (2017.08); *G01N 27/308* (2013.01)

(58) Field of Classification Search
CPC ..... C01B 32/21; C01B 32/194; C01B 32/174; C01B 32/156; C07C 201/12; G01N 27/308
USPC ................................................ 568/929, 930
See application file for complete search history.

(56) References Cited

U.S. PATENT DOCUMENTS

| | | | |
|---|---|---|---|
| 6,645,455 B2 | 11/2003 | Margrave et al. | |
| 7,125,533 B2 | 10/2006 | Khabashesku et al. | |
| 7,220,795 B2 | 5/2007 | Miyoshi et al. | |
| 7,339,160 B2 | 3/2008 | Raghuraman et al. | |
| 2003/0065206 A1* | 4/2003 | Bolskar .................. | B82Y 30/00 558/87 |
| 2003/0095914 A1 | 5/2003 | Belmont et al. | |
| 2003/0206026 A1 | 11/2003 | Diakonov et al. | |
| 2006/0054501 A1 | 3/2006 | Jiang et al. | |
| 2007/0065337 A1 | 3/2007 | Jiang et al. | |
| 2007/0272552 A1 | 11/2007 | Jiang et al. | |
| 2008/0060175 A1 | 3/2008 | Barvosa-Carter et al. | |
| 2009/0178921 A1 | 7/2009 | Lawrence et al. | |
| 2012/0059198 A1* | 3/2012 | Zou ........................ | B82Y 30/00 568/930 |

FOREIGN PATENT DOCUMENTS

| | | |
|---|---|---|
| JP | 2005263795 A | 9/2005 |
| KR | 20080109318 A | 12/2008 |
| WO | 2004005397 A1 | 1/2004 |
| WO | 2005066618 A1 | 7/2005 |

OTHER PUBLICATIONS

Borondics ("Functionalization of Carbon Nanotubes via Dissolving Metal Reductions" Journal of Nanoscience and Nanotechnology, 7, 1551-1559, 2007).*
Ren ("Aligned Carbon Nanotubes: Chapter 1, Introduction to Carbon" Nanoscience and Technology, DOI: 10.1007/978-3-642-30490-3_1, © Springer-Verlag Berlin Heidelberg 2013, p. 1-6).*
Evans (pKa Table, p. 1-6, dated Nov. 4, 2005, downloaded from http://evans.rc.fas.harvard.edu/pdf/evans_pKa_table.pdf on Mar. 19, 2017).*
Kim ("Electrochemical Oxidation of Benzene at a Glassy Carbon Electrode" Journal of Applied Electrochemistry 30, p. 543-549, 2000) (Year: 2000).*
Sijbesma ("Synthesis of a Fullerene Derivative for the Inhibition of HIV Enzymes" J. Am. Chem. Soc., 1993, 115, p. 6510-6512) (Year: 1993).*
Sukeguchi ("New diarylmethanofullerene derivatives and their properties for organic thin-film solar cells" Beilstein Journal of Organic Chemistry, vol. 5, 2009, p. 1-10; doi:10.3762/bjoc.5.7) (Year: 2009).*
Nezakati ("Different Functionalization Methods of Carbon Based Nanomaterials" Chemical Functionalization of Carbon Nanomaterials Chemistry and Applications, 2016, p. 29-57) (Year: 2016).*
Herrero ("Recent Advances in Covalent Functionalization and Characterization of Carbon Nanotubes" Handbook of Carbon Nano Materials, vol. 1, 2011, p. 271-323) (Year: 2011).*
Liu et al., "Grafting of diaminoalkane on glassy carbon surface and its functionalization", Electrochem. Commun., vol. 2, No. 10, 2000, pp. 707-712.
Maggini et al., "Addition of azomethine ylides to C60: synthesis, characterization, and functionalization of fullerene pyrrolidines", Journal of the American Chemical Society, vol. 115, No. 21, 1993, pp. 9798-9799.
International Search Report and Written Opinion for PCT/IB2010/000293, dated Nov. 16, 2010.
Masheter et al., "Investigating the reactive sites and the anomalously large changes in surface pK a values of chemically modified carbon nanotubes of different morphologies", Journal of Materials Chemistry, vol. 17, No. 25, 2007, pp. 2616-2626.
Masheter et al., "Voltammetric and X-ray photoelectron spectroscopic fingerprinting of carboxylic acid groups on the surface of carbon nanotubes via derivatisation with arylnitro labels", Journal of Materials Chemistry, vol. 17, No. 33, 2007, pp. 3515-3524.
Morlat-Therias et al., "Merrifield chemistry on electropolymers: protection/(photo)deprotection of amine functions", Chem. Commun., No. 11, 1998, pp. 1175-1176.
Oyama et al., "Introduction of Amine Functional Groups on Graphite Electrode Surfaces and their use in the Attachment of Ruthenium(II) to the Electrode Surface", J. Electroanal. Chem. Interfac. Electrochem., vol. 87, 1978, p. 435.
Pandurangappa et al., "Homogeneous chemical derivatisation of carbon particles: a novel method for functionalising carbon surfaces", Analyst, vol. 127, No. 12, 2002, pp. 1568-1571.
Pittman et al., "Chemical Modification of Carbon Fiber Surfaces by Nitric Acid Oxidation followed by Reaction with Tetraethylenepentamine", Carbon, vol. 35, No. 3, 1997, pp. 317-331.
Prabakar et al., "Surface modification of amine-functionalised graphite for preparation of cobalt hexacyanoferrate (CoHCF)-modified electrode: an amperometric sensor for determination of butylated hydroxyanisole (BHA)", Anal. Bioanal. Chem., vol. 386(7-8), 2006, pp. 2107-2115.
Roberts, R.M.G., "Synthesis of ferrocenyl derivatives of anthracene", Journal of Organometalic Chemistry, vol. 388 (1-2), 1990, pp. 181-186.
Robinson et al., "Redox-Sensitive Copolymer: A Single-Component pH Sensor", Analytical Chemistry, vol. 78, No. 7, 2006, pp. 2450-2455.
Sandhyarani et al., "Current understanding fo the structure, phase transition and dynamics of self-assembled monolayers on two-and three dimensional surfaces", Int. Reviews in Physical Chemistry, vol. 22, No. 2, 2003, pp. 221-262.
Shim, M. et al., "Functionalization of Carbon Nanotubes for Biocompatibility and Biomolecular Recognition", Nano Letters, vol. 2, No. 4, Jan. 25, 2002, pp. 285-288.
Streeter et al., "A sensitive reagentless pH probe with a ca. 120 mV/pH unit response", Journal of Solid State Electrochemistry, vol. 8, No. 10, 2004, pp. 718-721.
Szunerits et al., "Direct amination of hydrogen-terminated boron doped diamond surfaces", Electrochem. Commun., vol. 8, No. 7, 2006, pp. 1185-1190.
Thorogood et al., "Identifying quinone-like species on teh surface of graphitic carbon and multi-walled carbon nanotubes using reactions

(56) References Cited

OTHER PUBLICATIONS with 2, 4-dinitrophenylhydrazine to provide a voltammetric fingerprint", New J. Chem., vol. 37, No. 6, 2007, pp. 958-965.
Vettorazzi et al., "Modifiedglassycarbonelectrodes obtained by electrochemicaltreatment. Effects on the heterogeneouselectrontransferkinetics of an adsorbedaromaticamine", Electrochim. Acta., vol. 44(2-3), 1998, pp. 345-352.
Vijaikanth et al., "Chemically modified electrode based on an organometallic model of the [FeFe] hydrogenase active center", Electrochem. Commun., vol. 7, No. 4, 2005, pp. 427-430.
Wei et al., "Reaction of C60F18 with diethyl bromomalonate: diversion of the Bingel reaction and formation of the first 18 annulenic fullerene", J. Chem. Soc. Perkin Trans., vol. 2, No. 1, 2002, pp. 41-46.
Wildgoose et al., "Abrasively Immobilised Multiwalled Carbon Nanotube Agglomerates: A Novel Electrode Material Approach for the Analytical Sensing of pH", ChemPhysChem, vol. 5, No. 5, 2004, pp. 669-677.
Wildgoose et al., "Chemically Modified Carbon Nanotubes for Use in Electroanalysis", Microchimica Acta, vol. 152, No. 3, 2006, pp. 187-214.
Wildgoose et al., "Graphite powder derivatized with poly-L-cysteine using "building-block" chemistry—a novel material for the extraction of heavy metal ions", J. Mater. Chem, vol. 15, 2005, pp. 2375-2382.
Wildgoose, G. et al., "Anthraquinone-derivatised carbon powder: reagentless voltammetric pH electrodes", Talanta, vol. 60, No. 5, Jul. 27, 2003, pp. 887-893.
Yantasee et al., "Electrophilic Aromatic Subtitutions of Amine and Sulfonate onto Fine-Grained Activated Carbon for Aqueous-Phase Metal Ion Removal", Sep. Sci. Technol., vol. 39, No. 14, 2004, pp. 3263-3279.
Ye et al., "Electrocatalytic O2 Reduction at Glassy Carbon Electrodes Modified with Dendrimer-Encapsulated Pt Nanoparticles", Journal of the American Chemical Society, vol. 127, No. 13, 2005, pp. 4930-4934.
Zanella et al., "Deposition of Gold Nanoparticles onto Thiol-Functionalized Multiwalled Carbon Nanotubes", Journal of Physical Chemistry B., vol. 109, No. 34, 2005, pp. 16290-16295.
Zhang et al., "Electrochemical behavior of a covalently modified glassy carbon electrode with aspartic acid and its use for voltammetric differentiation of dopamine and ascorbic acid", Anal. Bioanal. Chem., vol. 382, No. 7, 2005, pp. 1669-1677.
Zhang, J. et al., "Photoluminescence and Electronic Interaction of Anthracene Derivatives Adsorbed in Sidewalls of . Single-Walled Carbon Nanotubes", Nano Letters, vol. 3, No. 3, Feb. 12, 2003, pp. 403-407.
Allongue et al., "Covalent Modification of Carbon Surfaces by Aryl Radicals Generated from the Electrochemical Reduction of Diazonium Salts", Journal of the American Chemical Society, vol. 119, No. 1, 1997, pp. 201-207.
Andrieux et al., "Derivatization of Carbon Surfaces by Anodic Oxidation of Arylacetates: Electrochemical Manipulation of the Grafted Films", Journal of the American Chemical Society, vol. 119, No. 18, 1997, pp. 4292-4300.
Antoniadou et al., "Anion exchange activity of electrochemically bonded ethylene diamine on carbon fibres", Journal of Applied Electrochemistry, vol. 22, 1992, pp. 1060-1064.
Armstrong et al., "Rapid Modification of Graphite Electrodes by Surface-bound Chromium Complexes: Preparation of an Electrode for Direct (unmediated) Electrochmistry of the Blue Copper Protein, Plastocyanin", J. Chem. Soc., Chem. Commun., No. 18, 1985, pp. 1236-1237.
Barbier et al., "Electrochemical Bonding of Amines to Carbon Fiber Surfaces Toward Improved Carbon-Epoxy Composites", Journal of the Electrochemical Society, vol. 137, No. 6, Jun. 1990, pp. 1757-1764.
Bard et al., "Electrochemical Methods: Fundamentals and Applications", 2nd Edition, 2001, pp. 226-252, p. 275, pp. 293-301 & pp. 640-644.

Basiuk et al., "Green derivatization of carbon nanotubes with Nylon 6 and L-alanine", Journal of Materials Chemistry, vol. 16, No. 45, 2006, pp. 4420-4426.
Basiuk et al., "Interaction of Oxidized Single-Walled Carbon Nanotubes with Vaporous Aliphatic Amines", Journal of Physical Chemistry B., vol. 106, No. 7, 2002, pp. 1588-1597.
Buttry et al., "Immobilization of amines at carbon fiber surfaces", Carbon, vol. 37, No. 12, 1999, pp. 1929-1940.
Camps et al., "Efficient cyclopropanation of C60 starting from malonates", J. Chem. Soc., Perkin Trans, vol. 1, No. 11, 1997, pp. 1595-1596.
Coleman et al., "Functionalization of Single-Walled Carbon Nanotubes via the Binge Reaction", Journal of the American Chemical Society, vol. 125, No. 29, 2003, pp. 8722-8723.
Covington et al., "Definition of pH Scales, Standard Reference Values, Measurement of pH and Related Terminology", Pure & Appl. Chem., vol. 57, No. 3, 1985, pp. 531-542.
Czerw et al., "Organization of Polymers onto Carbon Nanotubes: A Route to Nanoscale Assembly", Nano Lett., vol. 1, No. 8, 2001, pp. 423-427.
Davis et al., "Modification of catechol polymer redox properties during electropolymerization in the prescence of . aliphatic amines", Electrochim. Acta., vol. 43(3-4), 1998, pp. 291-300.
Deinhammer et al., "Electrochemical Oxidation of Amine-Containing Compounds: a route to the surface modification of glassy carbon electrodes", Langmuir, vol. 10, No. 4, 1994, pp. 1306-1313.
Delamar et al., "Modification of Carbon Fiber Surfaces by Electrochemical Reduction of Aryl Diazonium Salts: Application to Carbon Epoxy Composites", Carbon, vol. 35, No. 6, 1997, pp. 801-807.
Downard, "Electrochemcially Assisted Covalent Modification of Carbon Electrodes", Electroanaysis, vol. 12, No. 14, 2000, pp. 1085-1096.
Downard et al., "Suppression of Protein Adsorption at glassy Carbon Electrodes Covalentfy Modification with Tetraethylene Glycol Diamine", Electroanalysis, vol. 11, No. 6, 1999, pp. 418-423.
Elliott et al., "Chemically modified carbon electrodes", Analytical Chemistry, vol. 48, No. 8, 1976, pp. 1247-1254.
Elshahawi et al., "Accurate measurement of the hydrogen sulfide content in formation fluid samples—case studies", SPE 94707—SPE Annual Technical Conference and Exhibition, Dallas, Texas, Oct. 9-Dec. 12, 2005, 12 pages.
Evans, "pKa Table of Inorganic and Oxo-Acids", Retrieved from Internet on May 28, 2014.
Fitzer et al., "Chemical Interactions between the Carbon Fibre Surface and Epoxy Resins", Carbon, vol. 18, No. 6, 1987, pp. 389-393.
Friedman et al., "Carbene by the Dehydrohalogenation of Methyl Chloride", Journal of the American Chemical Society, vol. 82, No. 21, 1960, pp. 5758-5759.
Friedman et al., "Dehydrohalogenation of simple alkyl halides by strong base; evidence of carbene intermediates, extent of #-elimination", Journal of the American Chemical Society, vol. 83, No. 2, 1961, pp. 492-493.
Combined Search and Examination Report for GB0904813.3, dated Aug. 3, 2009.
Guo et al., "Modification of a glassy carbon electrode with diols for the suppression of electrode fouling in biological fluids", Chem. Pharm. Bull, vol. 44, No. 4, 1996, pp. 860-862.
Hayes et al., "Preservation of NADH Voltammetry for Enzyme-Modified Electrodes Based on Dehydrogenase", Analytical Chemistry, vol. 71, 1999, pp. 1720-1727.
Herrman et al., "Achrial and Chiral Higher Adducts of C70 by Bingel Cyclopropanation", Helvetica Chimica Acta, vol. 82, No. 2, 1999, pp. 261-289.
Hirsch et al., "Fullerene Chemistry in Three Dimensions: Isolationof Seven Regioisomeric Bisadducts and Chiral Trisadducts of C60 and Di(ethoxycarbonyl) methylene", Angew. Chem. Int. Ed. Engl., vol. 33, No. 4, 1994, pp. 437-438.
Holzinger et al., "Sidewall Functionalization of Carbon Nanotubes", Angew. Chem. Int. Ed., vol. 40, No. 21, 2001, pp. 4002-4005.

(56) References Cited

OTHER PUBLICATIONS

Hummelen et al., "Preparation and Characterization of Fulleroid and Methanofullerence Derivatives", Journal of Organic Chemistry, vol. 60, 1995, pp. 532-538.

Iijima, "Helical Microtubules of Graphitic Carbon", Nature, vol. 354, 1991, pp. 56-58.

Kaljuand et al., "Experimental Gas-Phase Basicity Scale of Superbasic Phosphazenes", Journal of Physical Chemistry A., vol. 111, No. 7, 2007, pp. 1245-1250.

Kaljurand et al., "Extension of the Self-Consistent Spectrophotometric Basicity Scale in Acetonitrile to a Full Span of 28 pKa Units: Unification of Different Basicity Scales", Journal of Organic Chemistry, vol. 70, No. 3, 2005, pp. 1019-1028.

Kaljurand et al., "Self-Consistent Spectrophotometric Basicity Scale in Acetonitrile Covering the Range between Pyridine and DBU", Journal of Organic Chemistry, vol. 65, No. 19, 2000, pp. 6202-6208.

Kooi et al., "Electrochemical Modification of Single Carbon Nanotubes", Angew. Chem. Int. Ed., vol. 41, No. 8, 2002, pp. 1353-1355.

Lawrence et al., "Comparison of the Electrochemical Reactivity of Electrodes Modified with Carbon Nanotubes from Different Sources", Electroanalysis, vol. 17, No. 1, 2005, pp. 65-72.

Lawrence et al., "Electrochemical determination of hydrogen sulfide at carbon nanotube modified electrodes", Analytica Chimica Acta, vol. 517(1-2), 2004, pp. 131-137.

Lawrence et al., "Triple Component Carbon Epoxy pH Probe", Electroanalysis, vol. 19, No. 4, 2007, pp. 424-428.

Leventis et al., "Derivatised carbon powder electrodes: reagentless pH sensors", Talanta, vol. 63, No. 4, Jul. 8, 2004, pp. 1039-1051.

Liang et al., "A Convenient Route to Functionalized Carbon Nanotubes", Nano Letters, vol. 4, No. 7, Jun. 3, 2004, pp. 1257-1260.

Lin et al., "A DFT Study of the Amination of Fullerenes and Carbon Nanotubes: Reactivity and Curvature", Journal of Physical Chemistry B., vol. 109, No. 28, 2005, pp. 13755-13760.

Lin et al., "Polymeric Carbon nanocomposites from Carbon Nanotubes Functionalized with Matrix Polymer", Macromolecules, vol. 36(19), 2003, pp. 7199-7204.

Liu et al., "Fullerene Pipes", Science, vol. 280, 1998, pp. 1253-1256.

Bingel, Carsten, "Cyclopropylation of Fullerenes," Chem. Ber., 1993, 126, pp. 1957-1959.

Butler et al., "Ferrocenyl-substituted fluorescent anthracenes and anthraquinones", Tetrahedron Letters 45, 2004, pp. 467-472.

Examination Report for GB0904813.3, dated Mar. 8, 2012, 3 pages.

Examination Report for GB0904813.3, dated Jul. 23, 2012, 2 pages.

Hickman et al., "Molecular Self-Assembly of Two-Terminal, Voltammetric Microsensors with Internal References", Science, vol. 252, May 3, 1991, pp. 688-691.

Kooi, et al., "Elektrochemische Modifizierung einzelner Kohlenstoff-Nanoröhren", Angew. Chem., vol. 114(8), 2002, pp. 1409-1411.

Timmerman et al., "Fullerene-acetylene hybrids: Towards a novel class of molecular carbon allotropes", Tetrahedron, vol. 52, Issue 14, Apr. 1, 1996, pp. 4925-4947.

Williams, J. M., "Getting reliable On-Site H2S and CO2 Concentrations for anti-corrosion measures in gas wells", SPE 81495—Jun. 9-12, 2003, SPE 13th Middle East Oil Show & Conference, 9 pages, Society of Petroleum Engineers Inc.

\* cited by examiner

DERIVATISATION OF CARBON

CROSS-REFERENCE TO RELATED APPLICATIONS

This patent application claims priority, pursuant to 35 U.S.C. § 119(e), to U.S. Non-Provisional application Ser. No. 13/142,515 filed Nov. 23, 2011, entitled "Derivatisation of Carbon", which claims priority to International Application No. PCT/11310/00293 filed Feb. 12, 2010, which claims priority to United Kingdom Application No. 0904813.3 filed Mar. 20, 2009, and the disclosures of which are fully incorporated herein by reference.

FIELD OF THE INVENTION

This invention relates to the derivatisation of carbon, i.e. to the covalent attachment of molecules to the surface of elemental carbon.

BACKGROUND OF THE INVENTION

Derivatisation of carbon surfaces has attracted considerable interest in recent years, in particular in connection with attaching molecules to carbon nanotubes.

The derivatisation of carbon may be carried out for a range of purposes which include modification of the surface properties of a carbon substrate, preparation of carbon-epoxy composites and attaching a molecule to a carbon electrode so that it can take part in an electrochemical reaction in an electrochemical sensor or an electrochemical catalyst.

Traditionally, carbon surfaces were modified by vigorous oxidation on the surface leading to the formation of carboxylic, quinonic, ketonic or hydroxylic groups, which were then reacted further with the target molecule. This aggressive process was difficult to control.

A number of procedures have been described for electrochemical induced derivatisation leading to the formation of a single covalent bond between a carbon electrode and a moiety which becomes attached. Examples have included:
electro-oxidation of alcohols, —see Gou et al Chem. Pharm. Bull., vol 44, page 860 (1996);
electro-oxidation of primary and secondary amines—see Barbier et al J. Electrochem. Soc., vol 137, page 135 (1990), Antoniadou et al J. Appl. Electrochem., 1992, vol 22, page 1060 (1992) and Deinhammer et al Langmuir vol 10 page 1306 1994);
electro-oxidation of carboxylates—see C. P. Andrieux et al, J. Am. Chem. Soc., vol 119, page 4292 (1997);
electro-oxidation of hydrazides—see M. A. Hayes and W. G. Kuhr, Anal. Chem., vol 71, page 1720 (1999); and
electro-reduction of diazonium salts—see P. Allongue et al J. Am. Chem. Soc., vol 119, page 201 (1997).

One approach to derivatisation of carbon without electrochemistry is the homogeneous reduction of diazonium compounds in reducing media—see Pandurangappa et al Analyst, vol 127, page 1568 (2002) and Leventis et al, Talanta vol 63, page 1039 (2004). Also in this category is WO2005/066618 (Schlumberger) which describes the diazocoupling of anthraquinonyl and nitrophenyl groups onto carbon nanotubes by means of the reduction of diazonium salts.

U.S. Pat. No. 6,645,455 (William Rice University) discloses derivitisation of carbon nanotubes by exposure to fluorine gas, possibly followed by further reaction to replace fluorine with some other group. Derivatisation of carbon nanotubes has also been carried out using amines or thiols to attach at defect sites of the carbon nanotubes—see Basiuk et al J Phys Chem B vol 106 age 1588 (2002) and Zanella et al J Phys Chem B vol 109 page 16290 (2005). A number of rather esoteric species have been reacted with carbon nanotubes: amongst these are reaction with nitrenes and the attachment of dipyridyl imidazolidene which is an unusual molecule in which a carbene forms part of a large delocalized system and in consequence does not undergo normal carbene reactions, see Holzinger et al Angewandte Chemie. Int Ed vol 40 page 4002 (2001).

SUMMARY OF THE INVENTION

We have now found a new and versatile method of attaching molecules to elemental carbon. In a first aspect this invention provides a process which comprises exposing a carbon substrate to an aprotic reaction mixture containing a strong base and a compound (herein referred to as the derivitising compound) with a general formula

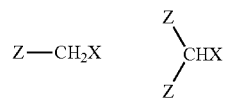

or in which X denotes a covalently attached leaving group capable of forming an X⁻ anion and each Z is a covalently attached moiety other than X comprising a plurality of atoms, which remains attached and does not have a hydrogen atom directly attached at the alpha position, i.e. does not have a hydrogen atom directly attached to the atom which itself is attached to —CH$_2$X or —CHX.

Without wishing to be bound by theory, we believe that the strong base detaches a hydrogen atom from the terminal —CH$_2$X or —CHX. The atom or group X then leaves as the anion X⁻ so that the compound is converted to a reactive carbene species having the general formula:

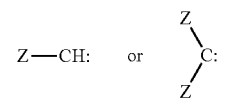

which then reacts with the carbon substrate. This reaction scheme is illustrated in FIGS. 1 and 2 of the accompanying drawings. If X is halogen, the removal of H and X from —CH$_2$X or —CHX can be classified as a 1,1 dehydrohalogenation reaction.

The base needs to be strong enough to remove a covalently bonded hydrogen atom from the derivitising compound. The derivitising compound must not have hydrogen attached to an atom which is in the alpha position, directly adjacent to the terminal —CH$_2$X or —CHX, so that the base cannot take hydrogen from this atom, hence leading to formation of a double bond rather than a carbene.

The strong base may be an uncharged, strongly basic compound and preferably it is a nitrogenous base. Two strong nitrogen-containing organic bases which are commercially available and which can be used in the process of this invention are 1,8-diazabicyclo[5.4.0]undec-7-ene (hereafter referred to as DBU) which has the formula

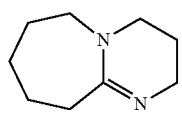 [SMILES: C1CCC2=NCCCN2CC1]

and its homologue 1,5-diazabicyclo[4.3.0]non-5-ene (hereafter DBN) which has the formula

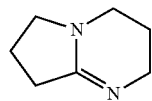

The strong base used in the process of this invention may therefore be an uncharged compound with a pKa which is at least as high as that of DBN in an aprotic solvent. The pKa values of numerous bases in acetonitrile as solvent have been reported by Kaljurand and coauthors, see Kaljurand et al J. Org. Chem vol 65 pp 6202-6208 (2000), Kaljurand et al J Org Chem vol 70 pp 1019-1028 (2005) and Kaljurand et al J Phys Chem B vol 111 pp 1245-50 (2007).

DBU has a reported pKa value in acetonitrile of 24.34 which is well above the reported pKa of 18.82 for triethylamine in the same solvent, see Kaljurand et al J Org Chem vol 70 pp 1019-1028 (2005). DBN has been reported to have a pKa slightly below that of DBU: the values reported by Leffek et al in Can J. Chem vol 67 pp 590-595 (1989) were 23.9 and 23.4 for DBU and DBN respectively.

The base used in the process of this invention may therefore be defined as a base having a pKa in acetonitrile of at least 22 or alternatively may be defined as having a pKa in acetonitrile which is at least equal to that of DBN in acetonitrile.

A number of nitrogen-containing and phosphorus-containing bases are known to have higher pKa values than DBU and could be used in the process of this invention. The papers by Kaljurand et al mentioned above provide references to many of these very strong bases.

Provided the strong base is a liquid, the process may be carried out using the strong base itself as reaction solvent. Alternatively the process may be carried out in an aprotic solvent such as toluene. The reaction may be carried out at a temperature of 0° C. or above, such as in the range from 0 to 40° C., preferably from 10 to 30° C.

The amount of strong base will generally be at least the stoichiometric amount needed to remove HX from the derivitising compound which is to be attached to carbon. An excess of base may be used.

This process is versatile in that a very great range of compounds may be used as the derivitising compound which is attached to a carbon substrate. The requirement for a strong base can be met using DBU or DBN which are commercially available reagents and the process can be carried out under ambient temperature conditions.

The moiety Z (or both moieties Z) in the derivitising compound must remain covalently attached to the terminal —CH: or >C: of the carbene species and so the formation of the leaving anion should be favoured over any formation of a Z anion. Preferably each moiety Z provides a carbon atom at the position alpha to the terminal —CH: or >C: i.e. provides a carbon atom which is directly covalently attached to the carbon of the terminal —CH: or >C: entity.

The derivatising compound used in the process of this invention may have any of the following five general formulae

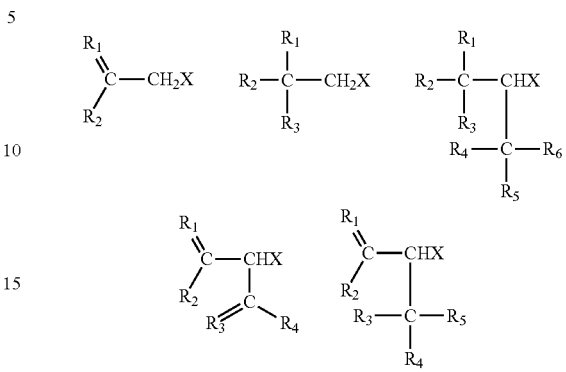

wherein $R_1$ to $R_6$ each independently denote attached groups, or two or more of the groups $R_1$ to $R_6$ may together form a ring.

These groups $R_1$ to $R_6$ may each independently be saturated or unsaturated aliphatic or cycloaliphatic (i.e. alicyclic) or may be aromatic. They may be substituted, and so an aromatic group may have one or more aliphatic, cycloaliphatic or aromatic substituents on it and an aliphatic or cycloaliphatic group may have one or more aromatic, aliphatic or cycloaliphatic substituents on it. Aliphatic groups may be straight or branched. These groups $R_1$ to $R_6$ may include hetero atoms such as nitrogen or silicon and they may be complexed with one or more metal atoms.

If two of the groups $R_1$ to $R_6$ form a ring, this ring may be aromatic. Thus a compound of the above general formula

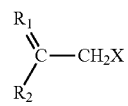

may have an aromatic ring formed by the groups $R_1$ and $R_2$. Examples of such compounds are

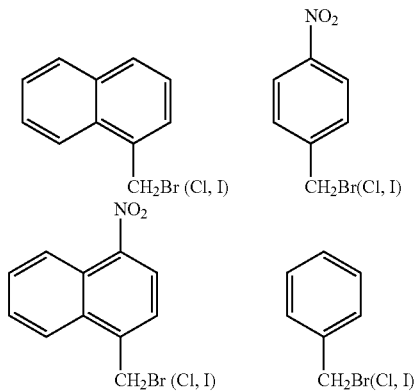

The part of the derivatising compound which becomes attached to the carbon substrate should generally be stable in the presence of the strong base, although it is possible that it would itself undergo another chemical reaction in the presence of that base. For example the strong base might remove a protecting group at the same time as carrying out the process of this invention.

The leaving group X is preferably a bromine, chlorine or iodine atom, but it may be some other leaving group. It may be a single atom or a group which contains a plurality of atoms. Preferably it is at least as good a leaving group as a chlorine atom. This may be defined by reference to the pKa of the acid HX (in water or other solvent) which should be no greater than the pKa of HCl in the same solvent. Leaving groups which are as good as or better than a chlorine atom include bromine, iodine, para-toluene sulphonate and trifluoroacetate.

The relative ratio of the carbon substrate and the compound which is to be attached to it may vary considerably. Generally the amount of the compound will be insufficient to attach to all possible binding sites on the surface of the carbon substrate.

The carbon substrate may be any form of carbon including glassy carbon, carbon fibres, carbon black and graphite or carbon paste, boron doped diamond and carbon epoxy. One further form of carbon, to which the invention may be applied, is the carbon nanotube (CNT) which was discovered in 1991. The structure of carbon nanotubes approximates to rolled-up sheets of graphite and can be formed as either single or multi-walled tubes. Single-walled carbon nanotubes (SWCNTs) constitute a single, hollow graphite tube. Multi-walled carbon nanotubes (MWCNTs) on the other hand consist of several concentric tubes fitted one inside the other.

The carbon substrate may be conductive and may be for use in an electrode. Forms of conducting carbon used in electrode manufacture are glassy carbon, carbon fibres, carbon black, various forms of graphite, carbon paste, boron doped diamond and carbon epoxy. Carbon nanotubes may also be used as part of an electrode and may be immobilized on the surface of another form of conducting carbon.

As indicated at the beginning, carbon which has been derivatised by the attachment of a molecular species may be used for a variety of purposes. Carbon which has been derivatised by the process of this invention may be utilised for any such purposes. In particular, the Z—CH or $Z_2C$ moiety which becomes attached to carbon may be such that it can undergo electrochemical reduction or oxidation, so that the derivatised carbon can be used in an electrochemical sensor, for example in the manner described in WO 2005/66618, the disclosure of which is incorporated herein by reference. A reversible oxidation and reduction which can be monitored by voltammetry is particularly useful. This may be preceded by an initial irreversible alteration of the covalently attached moiety to form a species which is still covalently attached to the carbon substrate and can undergo reversible electrochemical reduction and oxidation.

This is exemplified below by covalent attachment of a nitrophenyl group whose nitro group can be reduced electrochemically to a nitroso group and thereafter reversibly reduced to a hydroxylamino group.

Embodiments of the invention will now be described with reference to the accompanying drawings and examples.

DETAILED DESCRIPTION

Figure 1:
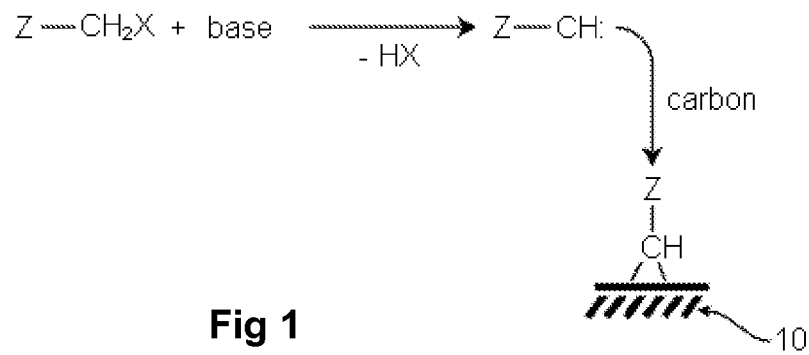
FIG. 1 shows the reaction scheme when the derivatising compound to be attached to a carbon substrate has the formula $Z—CH_2X$.
Figure 2:
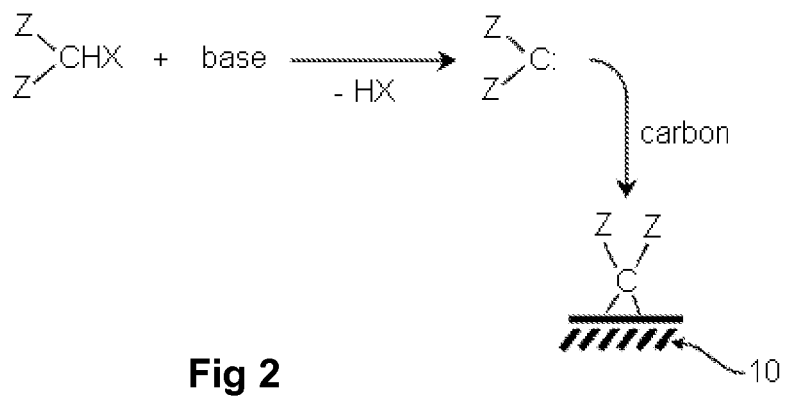
FIG. 2 shows the reaction scheme when the derivatising compound to be attached has the formula $Z_2—CHX$.

As shown in FIG. 1, the reaction is believed to consist of the base removing a hydrogen atom from the compound $Z—CH_2X$, causing X to leave as $X^-$ so that a carbene species Z—CH: is formed. This is able to react at the surface of a carbon substrate, so that the moiety Z—CH is attached to the substrate surface through two single carbon-carbon bonds. As shown by FIG. 2 the scheme is essentially the same if the compound to be attached is $Z_2—CHX$.

Several experiments were carried out in order to provide evidence for this reaction scheme.

Experiment 1

DBU and Deuterochloroform 1 ml DBU and 2 ml $CDCl_3$ were quickly mixed in a 20 ml vial, which was then sealed with a butyl rubber septum. Heat was liberated, indicating that an exothermic reaction was taking place. The mixture turned yellow in 16 hours and became dark coloured and viscous in 2 to 3 days, after which time the adduct DBU.HCl was detected by NMR spectroscopy. It was confirmed by single crystal X-ray diffraction after isolating it

Experiment 2

DBU and Bromoform 1 ml DBU and 2 ml $CHBr_3$ were quickly mixed in a 20 ml vial, which was then sealed with a butyl rubber septum. The solution turned yellow immediately the reactants were mixed and reaction released a considerable amount of heat. The solution turned dark brown within 4 hours. DBU.HBr was detected by NMR spectroscopy.

The above experiments 1 and 2 showed that DBU was able to break carbon-hydrogen (and likewise carbon-deuterium) bonds in deuterochloroform and bromoform. The following three experiments demonstrate formation of carbene species.

Experiment 3

Formation of Dichlorocarbene and Capture with Cyclohexene 1 ml DBU, 2 ml $CDCl_3$ and 0.4 ml cyclohexene were quickly mixed in a 20 ml vial and then sealed with a butyl rubber septum. Several days later, after the solution had turned a dark brown colour, the mixture was analysed by headspace GC-MS.

7,7-dichloro-bicyclo[4,1,0]heptane was detected. The latter is the product obtained by reaction of dichlorocarbene at the double bond of cyclohexene. It appeared as a clear peak in the gas chromatogram and the mass spectrum for that peak included a molecular ion at mass 164.

Experiment 4

Formation of Dichlorocarbene and Capture with Tetramethylethylene 1 ml DBU, 2 ml $CDCl_3$ and 0.4 ml tetramethylethylene were quickly mixed in a 20 ml vial and then sealed with a butyl rubber septum. The solution turned a dark brown colour over several days, after which the mixture was analysed by headspace GC-MS and 3,3-dichloro-1,1,2,2-tetramethyl-cyclopropane was detected. The product 3,3-dichloro-1,1,2,2-tetramethylcyclopropane was observed as a sharp peak in the gas chromatogram which could be identified by the associated mass spectrum. This experiment once again confirmed the production of dichlorocarbene in the reaction of DBU with $CDCl_3$.

Experiment 5

Formation of Dibromocarbene and Capture with Cyclohexene 1 ml DBU, 2 ml $CHBr_3$ and 0.4 ml cyclohexene were quickly mixed in a 20 ml vial, which was then sealed with a butyl rubber septum. Upon mixing the mixture turned yellow immediately and after several days it had turned black. The mixture was examined by headspace GC-MS and 7,7-dibromo-bicyclo[4,1,0]heptane was detected. It was observed as a sharp peak in the gas chromatogram which was identified by the associated mass spectrum with a molecular ion at mass 256. This experiment confirmed that dibromocarbene was produced in the reaction of DBU with $CHBr_3$.

EXAMPLES

The following examples demonstrate the process of the invention being used to attach reactive moieties to carbon substrates. All chemicals were supplied by Aldrich and used without further purification.

Example 1

Attachment of 4-Nitrobenzyl Group onto Graphite

Figure 3:
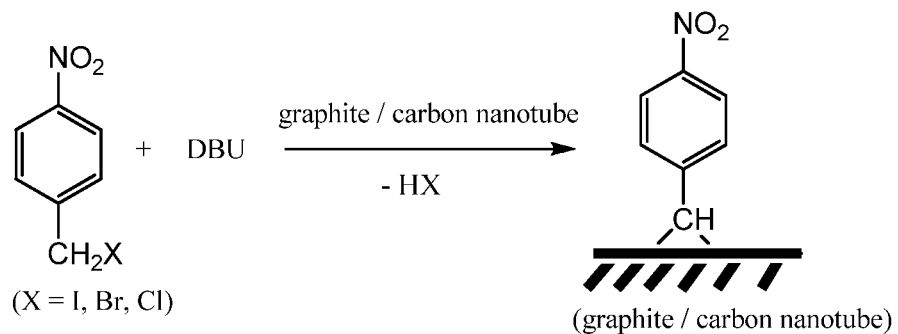
FIG. 3 shows a reaction scheme when the derivatising compound to be attached is 4-nitrobenzylbromide as in Examples 1 and 2.

This reaction is illustrated as FIG. 3 of the drawings. 4-nitrobenylbromide becomes nitrophenylmethylene moieties attached to carbon.

4-nitrobenzylbromide (1.4421 g, 6.68 mmol) supplied as a crystalline pale yellow powder was mixed with graphite (1.0182 g) in a 20 ml vial. DBU (1 ml) was added to the vial which was then sealed with a butyl rubber septum. The DBU acted as the required strong base and also provided the reaction solvent. The mixture was stirred at first, but after one day the mixture had solidified and could no longer to be stirred. Acetone was added to the mixture, then the solvent was filtered off and the graphite was washed repeatedly with acetone by filtration. Initially the acetone filtrate was dark brown but after repeated washing the acetone filtrate was colourless. The graphite which had been filtered off was allowed to dry in air.

The binding of nitrophenyl groups to graphite was demonstrated by mechanically immobilising the dried graphite on an electrode and examining its electrochemistry.

The dried graphite which had been derivatised with nitrophenyl groups was placed on a fine filter paper. A basal plane pyrollytic graphite (bppg) electrode was polished smooth on glass polishing paper and then on silicon carbide paper, after which the polished surface was gently rubbed on the dried graphite on the filter paper, so that this graphite became immobilised on the electrode. Cyclic voltammetry was then carried out using this electrode.

Figure 4:
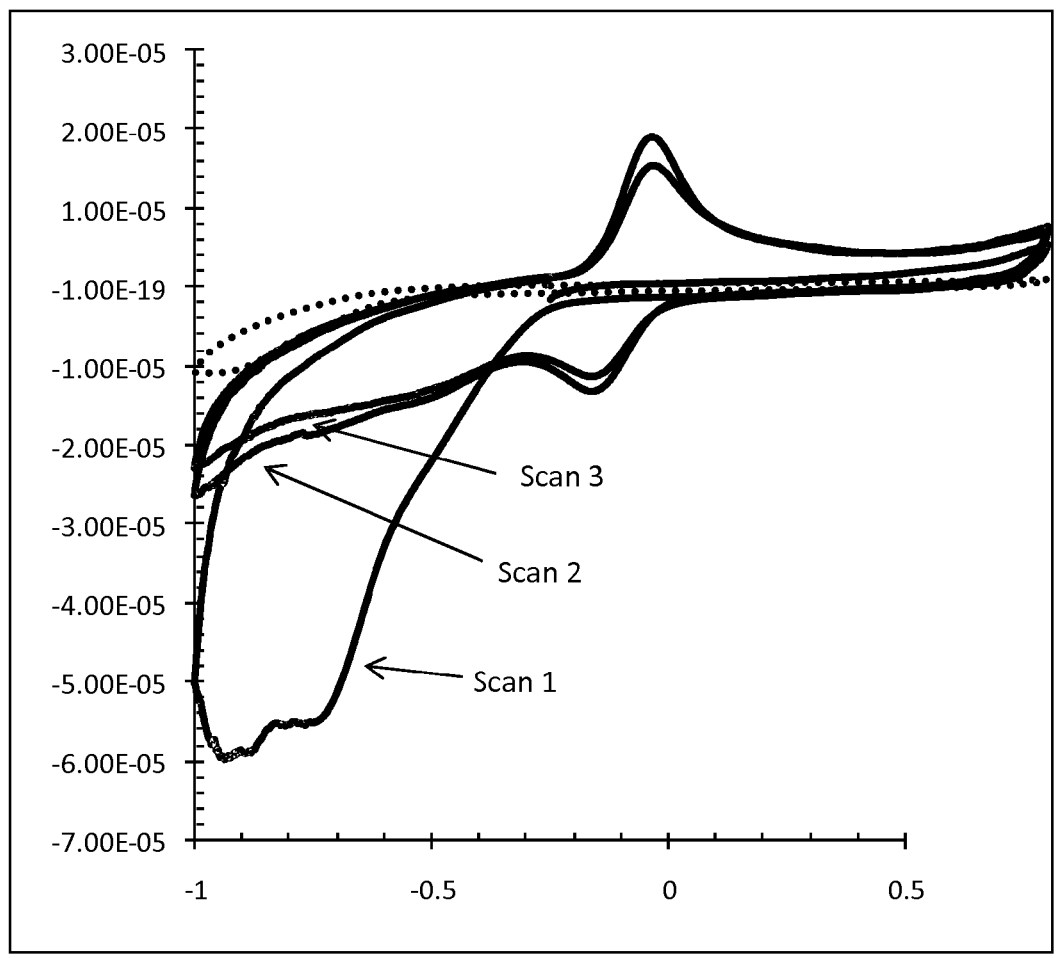
FIG. 4 shows voltammograms obtained in Example 1.

FIG. 4 shows the initial three repeat cyclic voltammograms (scan rate=100 mV $s^{-1}$) in a solution containing 0.1 M HCl. The voltammetry for a blank electrode without derivatised carbon is shown dotted. On the first cycle a single large reduction wave is observed at −0.50 V. The potential was then reversed at −0.60 V and swept in an oxidative direction. This produced an oxidation wave at +0.39 V. The subsequent reduction sweep showed a new reductive process at +0.29 V corresponding to the reduction of the oxidised species at +0.39 V. It can also be seen that the reduction wave at −0.50 V has diminished in the second cycle showing that the nitrophenyl groups present on the electrode surface had undergone a permanent electrochemical reduction.

Figure 5:
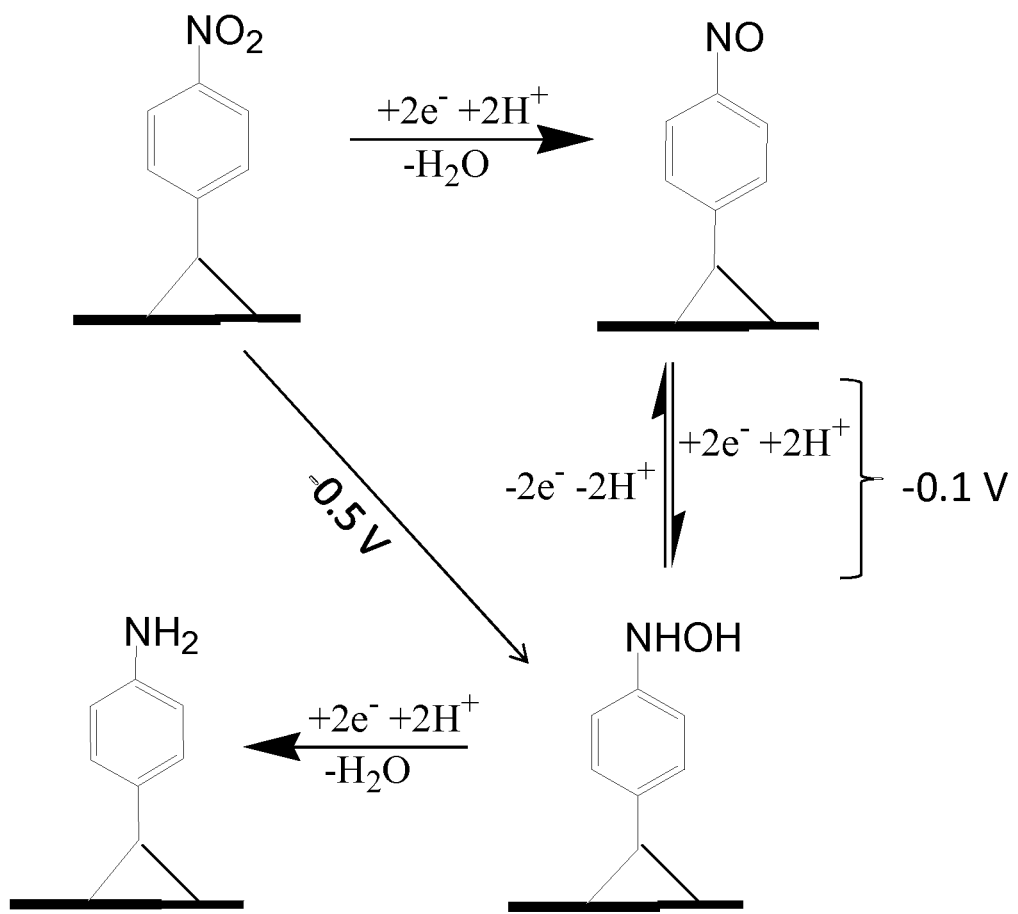
FIG. 5 shows the redox reaction scheme for the derivatised carbon of Examples 1 and 2.

The reduction process at −0.5 V was attributed to the nitrophenyl group undergoing a 4 electron, 4 proton reduction to form the corresponding hydroxylamine species as shown in the reaction scheme which is FIG. 5 of the drawings. The new oxidative wave at +0.39 V was assigned to the oxidation of the newly formed hydroxylamine entity back to the nitrosophenyl species. This nitrosophenyl species was then reduced back to the hydroxylamine on the subsequent reduction scan at +0.29 V.

Plots of oxidation and reduction peak current, measured at +0.39 V and +0.29 V respectively, against scan rate were found to be linear from 25 to 400 mV $s^{-1}$. These results showed that the 4-nitrophenyl group was strongly attached to the carbon surface. Further evidence to show that the nitrophenyl group had been immobilised onto the carbon was obtained by exchanging the buffer solution with a fresh solution and recording the voltammetry again. The voltammetric waveshapes (not shown) for each response were similar to those obtained previously, thereby confirming that the nitrophenyl group was attached to the graphite particles.

The stability of the electrode was further tested by placing it in fresh buffer solution and repetitively cycling over the voltage scan range. It was observed that although there was a 50% loss in peak current over the first 50 cycles, the peak current and voltammetric response were almost constant for the next 100 cycles, indicating strong attachment to the graphite.

As a control experiment the derivatisation procedure was carried out without DBU. Acetone was substituted as the solvent. The reaction mixture was stirred at room temperature for 2 days. The solvent was filtered off, and the graphite was washed with acetone by filtration several times until the acetone filtrate was colourless. The resulting graphite was dried in air. Testing as above did not show the redox behaviour described above, indicating that attachment of nitrophenyl groups to graphite had not occurred in this control experiment.

Example 2

Attachment of 4-Nitrobenzyl Groups onto Carbon Nanotubes (CNTs)

As with the previous example, the scheme of the reaction is shown in FIG. 3. Crystalline pale yellow powder 4-nitrobenzylbromide (1.4347 g, 6.64 mmol) was mixed with carbon nanotubes (117.76 mg) in a 20 ml vial. Into the vial was added 3 ml DBU while stirring, and the vial was then sealed with a butyl rubber septum. The mixture quickly solidified and could no longer be stirred. After this reaction had taken place, acetone was added to the mixture, the solids were filtered off and washed with acetone by filtration. The acetone filtrate was at first red brown colored. Washing was repeated until the acetone filtrate was colourless. The recovered carbon nanotubes were then allowed to dry whilst exposed to the air.

The binding of nitrophenyl groups to carbon nanotubes was demonstrated by immobilising the dried carbon nanotubes on a glassy carbon electrode and examining its electrochemistry. Before immobilizing on an electrode, the derivatised carbon nanotubes (1 mg) were washed again using DMF (N,N-dimethylformamide) for many times by centrifugation until the DMF supernatant was colorless. An immobilising suspension was prepared by introducing 1 mg of carbon nanotubes into 1 mL of DMF.

The liquid was then sonicated for 20 minutes to aid in the dispersion of the carbon. A 20 μL aliquot of the sonicated suspension was then placed directly onto the glassy carbon surface and left to dry. The electrode was then ready for use.

Figure 6:
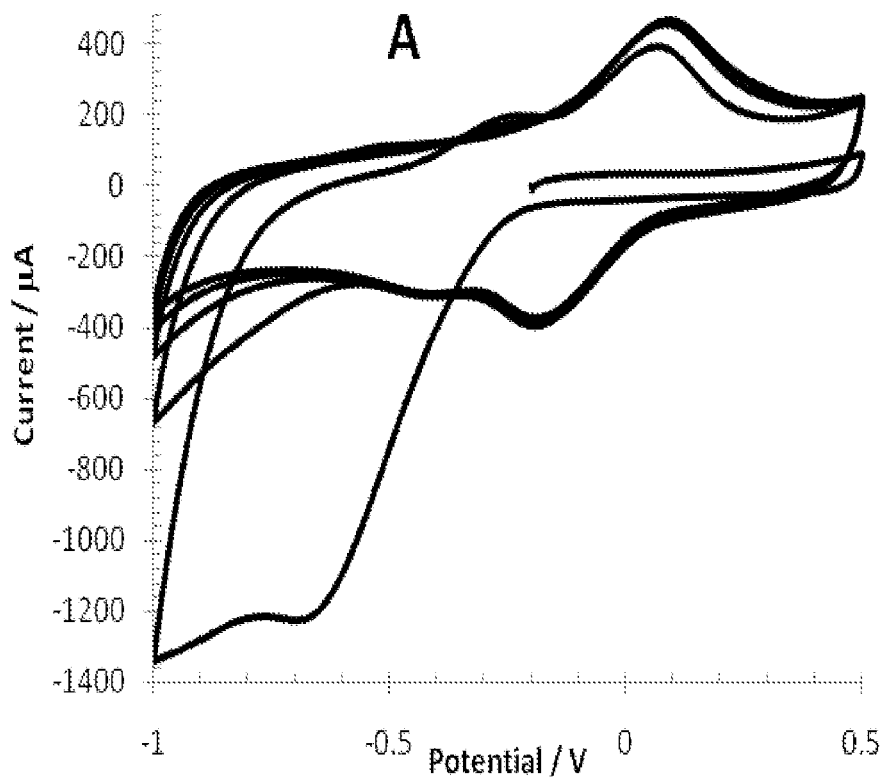
FIG. 6 shows voltammograms obtained in Example 2.

Cyclic voltammetry was then carried out. FIG. 6 details the initial five cyclic voltammograms of the 4-nitrobenzylbromide derivatised carbon nanotubes in pH 7 phosphate buffer as the potential was repetitively cycled over a wide potential range (−0.2 to +0.6 V to −1 V) at a scan rate of 0.1 Vs$^{-1}$. The first oxidative sweep produced no well defined voltammetric signals, but upon reversal of the scan a reductive wave was observed at −0.8 V, consistent with the reduction of the nitro group to the corresponding hydroxylamine species in accordance with the reaction scheme of FIG. 5. Upon initiating the second voltammetric scan a new oxidation wave was observed at 0.0 V, which had a corresponding reduction wave at −0.2 V. The form of the sequence of voltammograms is consistent with the oxidation of hydroxylamine species to the corresponding nitroso compound (FIG. 5). These results therefore demonstrate the presence of nitrophenyl species upon the surface of the carbon nanotubes.

Subsequently the potential scan was narrowed to examine only the voltammetric response of the hydroxylamine/nitroso redox couple, and various scan rates were used. As the scan rate was increased from 0.025 V to 0.4 V, an increase in the oxidative and reductive peak current was observed. A plot of peak current against scan rate was found to be linear over the entire scan rate studied indicating that the nitrophenyl species is attached to the surface of the carbon nanotubes.

In a further experiment, the square wave voltammetric response of these nitrobenzyl-derivatised carbon nanotubes was examined in buffer solutions with various pH values. As the pH was varied from 4 to 9 the oxidative peak potential for the oxidation of hydroxylamine to the nitroso species increased. A plot of peak potential versus pH was found to be linear with a gradient of 52.2 mV/pH unit consistent with a 2 electron, 2 proton transfer as illustrated for the hydroxylamine/nitroso redox couple in FIG. 5.

Again the fact that the electrode can be successfully removed, washed and placed into various buffer solutions shows that the species undergoing electrochemical oxidation and reductions is attached to the carbon nanotubes.

In a control experiment 4-nitrobenzylbromide (1.3826 g) was mixed with carbon nanotubes (123 mg) in ca. 3 ml acetone but without the presence of DBU. The reaction mixture was stirred at ambient temperature for 2 days. The acetone was filtered off and was pale yellow in colour. The remaining solid was washed with acetone several times more by filtration until the acetone filtrate was colourless. The acetone filtrate was evaporated and almost all of the 4-nitrobenzylbromide was recovered. The CNTs which had been used in this experiment were immobilised on a glassy carbon electrode in the same manner as described above. The voltammetric response of these carbon nanotubes did not show the redox couple at 0.0 V, indicating that there is no hydroxylamine or nitroso species present on the surface and hence that derivatisation of the CNTs had not taken place.

Example 3

Attachment of 2,4-dinitrobenzylbromide to Graphite

Figure 7:
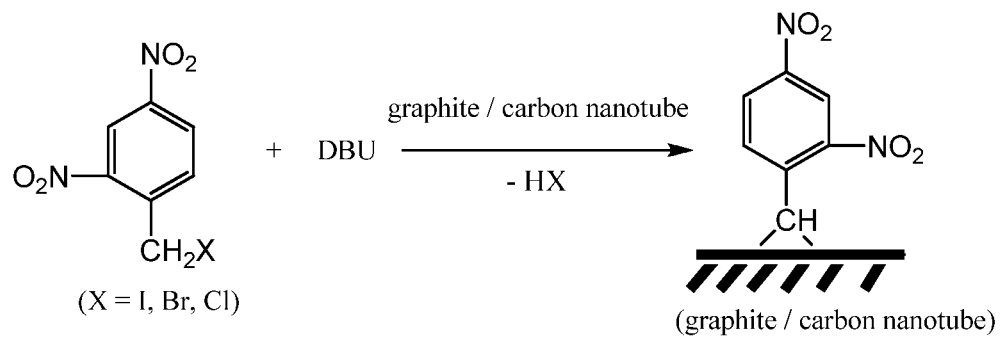
FIGS. 7, 8 and 9 show reaction schemes with other derivatising compounds.

The scheme of this reaction is illustrated as FIG. 7. Graphite powder (115 mg, 9.57 mmol) and 2,4-dinitrobenzyl bromide (267 mg, 1.02 mmol) were suspended in toluene (3 ml) in a 20 ml reaction vial and cooled in an ice bath. DBU (1 ml, 6.6 mmol) was added drop wise over ca. 10 mins. The vial was sealed with a butyl rubber septum and the resultant purple suspension stirred at ambient temperature overnight. The liquid was filtered off and the remained solid was washed with toluene by filtration several times. After this, the solid was washed with N,N-dimethylformamide using a centrifuge until the supernatant was colourless. The solid was dried at ambient temperature overnight and then at 120° C. for 6 hours. A control experiment was also carried out, using the same procedure, but omitting the DBU.

The derivatised graphite, graphite from the control experiment, and untreated graphite were all immobilised on glassy carbon electrodes using the procedure of the previous example (except that acetone was used in place of DMF). The derivatised graphite showed a large reductive wave at −0.8 V followed by emergence of a new redox wave at 0.0 V. By contrast, these features were not seen in the voltammetric response of graphite from the control experiment which was the same as that of untreated graphite.

Figure 8:
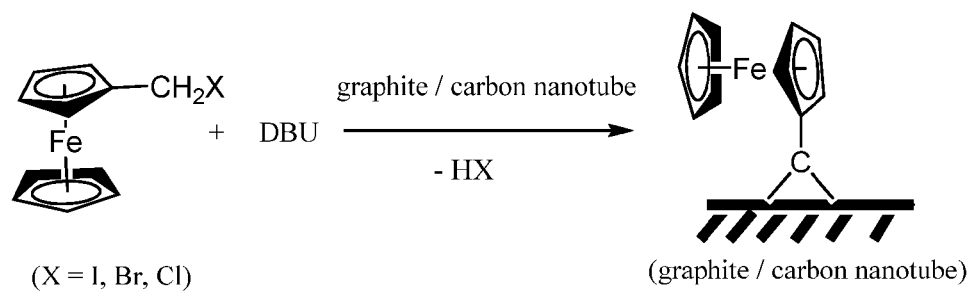
Figure 9:
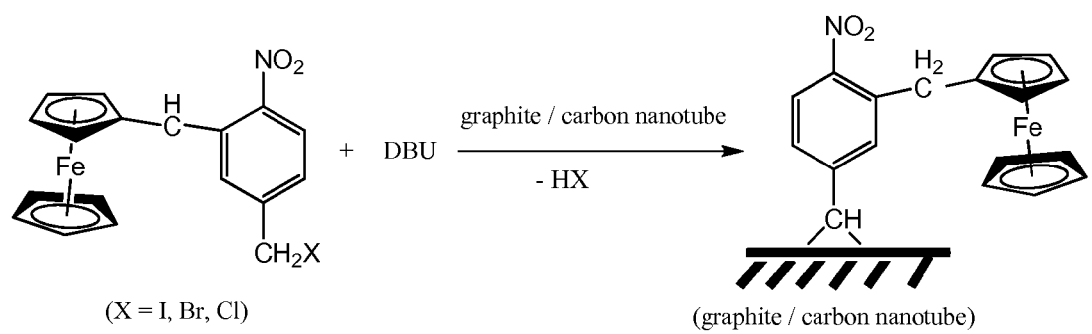

The procedures described in the above examples could also be used for attaching a variety of other species to various forms of carbon, including carbon nanotubes. The attached species could be redox active. One possibility is to attach ferrocene as illustrated in FIG. 8 or a moiety containing both ferrocene and nitrophenyl as illustrated in FIG. 9. The nitrophenyl group would then provide a pH-sensitive redox active species, while the ferrocene would provide a reference species, insensitive to pH.

The invention claimed is:

1. A process for attaching molecules to elemental carbon comprising reacting an elemental carbon substrate with an aprotic reaction mixture containing a base and a compound with a general formula of

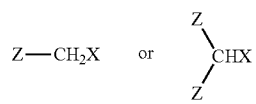

in which X denotes a covalently attached atom or group capable of forming an X$^-$ anion; and
—CH$_2$X or —CHX group; and wherein reacting the an elemental carbon substrate with the aprotic reaction mixture produces elemental carbon with

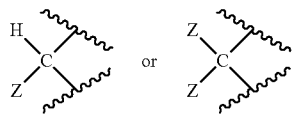

attachments.

2. The process of claim 1 wherein the compound has the general formula

3. The process of claim 1 wherein the compound is one of the following

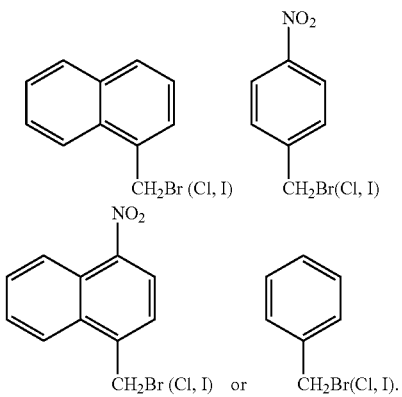

4. The process of claim 1 wherein the base is an organic compound containing nitrogen.

5. The process of claim 1 wherein the pKa of the base, in acetonitrile as solvent, is at least 22.

6. The process of claim 1 wherein the pKa of the base, in acetonitrile as solvent, is at least as high as that of 1,5-diazabicyclo[4.3.0]non-5-ene.

7. The process of claim 1 wherein the base is either 1,5-diazabicyclo[4.3.0]non-5- ene or 1,8-diazabicyclo [5.4.0]undec-7-ene.

8. The process of claim 1 wherein X is such that the pKa of the acid HX in water is no greater than the pKa of HCl in water.

9. The process of claim 1 wherein X is chlorine, bromine or iodine.

10. The process of claim 1 wherein the elemental carbon substrate is carbon nanotubes.

11. The process of claim 1 wherein the elemental carbon substrate is graphene.

12. The process of claim 1 wherein the

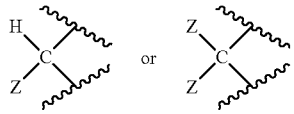

groups which becomes attached to the elemental carbon substrate can subsequently undergo one or more electrochemical reductions or oxidations.

* * * * *